(12) United States Patent
Sasaki et al.

(10) Patent No.: US 7,132,561 B2
(45) Date of Patent: Nov. 7, 2006

(54) PROCESS FOR PRODUCING FLUORINATED DICYANOBENZENE

(75) Inventors: Toru Sasaki, Fukushima (JP);
Tetsuhiro Furukawa, Fukushima (JP);
Yoshinori Sato, Fukushima (JP);
Takuji Yamamoto, Fukushima (JP);
Takashi Yoneyama, Fukushima (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/398,443

(22) PCT Filed: Oct. 3, 2001

(86) PCT No.: PCT/JP01/08718

§ 371 (c)(1),
(2), (4) Date: Apr. 4, 2003

(87) PCT Pub. No.: WO02/28822

PCT Pub. Date: Apr. 11, 2002

(65) Prior Publication Data

US 2004/0030173 A1    Feb. 12, 2004

Related U.S. Application Data

(60) Provisional application No. 60/256,915, filed on Dec. 21, 2000.

(30) Foreign Application Priority Data

Oct. 4, 2000 (JP) .............................. 2000-305036
Sep. 3, 2001 (JP) .............................. 2001-265573

(51) Int. Cl.
*C07C 255/04* (2006.01)
(52) U.S. Cl. ..................................................... 558/419
(58) Field of Classification Search ................. 558/419
See application file for complete search history.

(56) References Cited

U.S. PATENT DOCUMENTS

| | | | |
|---|---|---|---|
| 3,290,353 A | 12/1966 | Bluestone et al. | |
| 3,975,424 A | 8/1976 | Fujii et al. | |
| 5,153,350 A * | 10/1992 | Braish | 558/419 |
| 6,020,517 A * | 2/2000 | Monzen et al. | 558/425 |
| 6,229,040 B1 | 5/2001 | Marhold et al. | |
| 6,462,218 B1 | 10/2002 | Hallenbach et al. | |

FOREIGN PATENT DOCUMENTS

| | | |
|---|---|---|
| EP | 0 120 575 A | 10/1984 |
| EP | 0 899 256 A2 | 3/1999 |
| WO | WO 87/07267 A | 12/1987 |

OTHER PUBLICATIONS

International Search Report, for PCT/JP01/08718, dated Dec. 16, 2002.
Search Report dated Oct. 18, 2005.

* cited by examiner

*Primary Examiner*—Golam M. M. Shameem
*Assistant Examiner*—Ebenezer Sackey
(74) *Attorney, Agent, or Firm*—Sughrue Mion, PLLC

(57) ABSTRACT

An object of the invention is to provide a process for industrially producing fluorinated dicyanobenzenes using tetrachlorodicyanobenzene as a raw material. According to the present invention, fluorinated dicyanobenzene can be produced in a high yield by allowing tetrachlorodicyanobenzenes to react with a fluorinating agent in the presence of a non-protonic polar solvent in an amount of 0.1 to 3 times by mass based on the tetrachlorodicyanobenzene. Further, the above production can be conducted more efficiently by reacting while disintegrating or removing bulk solid matters.

14 Claims, No Drawings

PROCESS FOR PRODUCING FLUORINATED DICYANOBENZENE

CROSS REFERENCE OF RELATED APPLICATION

This application is an application filed under 35 U.S.C. §111(a) claiming benefit pursuant to 35 U.S.C. §119(e) of the filing date of Provisional Application 60/256,915 filed on Dec. 21, 2000, pursuant to 35 U.S.C. §111(b).

DETAILED DESCRIPTION OF THE INVENTION

1. Technical Field

The present invention relates to a process for producing fluorinated dicyanobenzenes useful as an intermediate and raw material for preparation of medical and pharmaceutical products, agricultural chemicals and polymers. Particularly, tetrafluoroterephthalonitrile is important as an intermediate for agricultural chemicals.

2. Background Art

As a process for producing fluorinated dicyanobenzenes represented by the formula (2):

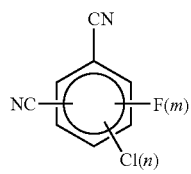

(2)

wherein m is an integer of 1 to 4, n is 0 or an integer of 1 to 3, and m+n=4, a process for production of allowing a substituted dicyanobenzene to react with a fluorinating agent is known.

For example, JP-B-44-28493/1969 and Bull. Chem. Soc. Jpn, 40, 688(1971) disclose a process for producing tetrafluoro terephthalonitrile by allowing tetrachloroterephthalonitrile to react with potassium fluoride in the absence of a solvent. This process, however, has an extremely high reaction temperature of 300° C. and a problem of corrosion of the reaction device. Further, it has a complicated process for isolating the product and a low yield of less than 80%, so that it is difficult to consider this process an excellent process industrially.

JP-A-60-112751/1985 discloses a process for producing tetrafluorophthalonitrile by allowing tetrachloro phthalonitrile to react with a fluorinating agent in the presence of a benzonitrile solvent. The process has a high yield of from 90 to 92%, but a high reaction temperature of about 300° C. so that there is a problem of corrosion of the reaction device. Further, the process requires the reaction to be carried out for 10 hours or more and thereby this process is hardly said to be an advantageous process industrially.

In the meantime, JP-A-51-6940/1976 and U.S. Pat. No. 3,975,424 disclose a process for preparing tetrafluoroterephthalonitrile by allowing tetrachloroterephthalonitrile to react with potassium fluoride in the presence of a polar solvent having a water content of not more than 0.2%. This process has a low reaction temperature of 130° C. and an excellent property such that the reaction is completed in a short time of 5 hours. This process, however, has a low yield of at most 81%, and in the process, the solvent is used in an amount of 7.7 times by mass or more based on tetrachloroterephthalonitrile which is a raw material. Accordingly, in the case of carrying out the process industrially, it is expected that its productivity is low and large amounts of wastes would be discharged. The above prior art, further, does not disclose a method of recovering the solvent used in the reaction or a reaction device employed in carrying out the process industrially.

As described above, when carried out industrially, conventional processes for producing fluorinated dicyanobenzene have problems that need to be solved, such as low yield and generation of large amounts of industrial wastes.

OBJECT OF THE INVENTION

It is an object of the invention to provide a process for industrially producing a fluorinated dicyanobenzene represented by the formula (2):

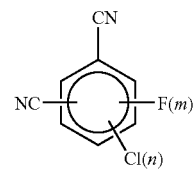

(2)

in the formula, m is an integer of 1 to 4, n is 0 or an integer of 1 to 3, and m+n=4, using, as a raw material, tetrachlorodicyanobenzene represented by the formula (1)

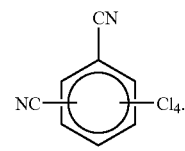

(1)

More specifically, in the processes for producing fluorinated dicyanobenzene by reacting tetrachlorodicyanobenzene with a fluorinating agent, it is an object of the invention to provide a process for producing a fluorinated dicyanobenzene in a high yield such that the reaction is carried out at a low temperature for a short time, which is unattained by conventional process.

Means to Solve the Problems

The present inventors reacted tetrachloro dicyanobenzene with a fluorinating agent using a non-protonic polar solvent and examined the effect of the amount of the non-protonic polar solvent on the reaction rate and the yield of fluorinated dicyanobenzene.

As a result, the present inventors unexpectedly found that by decreasing the non-protonic polar solvent amount to less than 3 times by mass per tetrachlorodicyanobenzene, fluorinated dicyanobenzenes can be produced not only at an improved reaction rate, but also at a higher yield at a higher purity, as compared with using the non-protonic polar solvent in an amount more than 3 times by mass.

Up to this time, by decreasing the solvent amount based on the tetrachlorodicyanobenzene, the yield of fluorinated dicyanobenzene was occasionally lowered. The present inventors found that by decreasing the amount of the non-protonic polar solvent to less than 3 times by mass based on the tetrachlorodicyanobenzene, the reaction mixture is wet powdery or creamy, but not liquid, so that when conventional reaction vessels equipped with a stirrer are used, bulk solid matters are generated in the reaction mixture or adhered to the wall surface of the reaction vessel, and when the amounts thereof are increased, the yield of the aimed fluorinated dicyanobenzene is lowered. The inventors further found that carrying out the reaction by disintegrating or removing the bulk solid matters, fluorinated dicyanobenzenes are preferably produced.

The present inventors have been accomplished the present invention based on the above described investigation and findings.

Namely, the present invention comprises the following items.

[1] The process for producing a fluorinated dicyanobenzene represented by the formula (2):

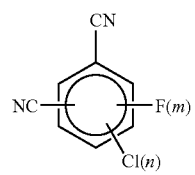
(2)

in the formula, m is an integer of 1 to 4, n is 0 or an integer of 1 to 3, and m+n=4, which process comprises allowing a tetrachlorodicyanobenzene represented by the formula (1)

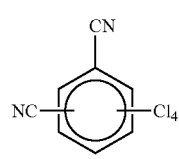
(1)

to react with a fluorinating agent in the presence of a non-protonic polar solvent in an amount of from 0.1 to 3 times by mass based on the tetrachlorodicyanobenzene.

[2] The process for producing a fluorinated dicyanobenzene according to [1] wherein the non-protonic polar solvent is an organic solvent comprising at least one selected from the group consisting of N,N-dimethyl formamide, dimethyl sulfoxide and N-methyl-2-pyrrolidone.

[3] The process for producing a fluorinated dicyanobenzene according to [1] wherein the non-protonic polar solvent is N,N-dimethyl formamide.

[4] The process for producing a fluorinated dicyanobenzene according to any one of [1] to [3] wherein the fluorinating agent is an alkali metal fluoride or alkaline earth metal fluoride.

[5] The process for producing a fluorinated dicyanobenzene according to [4] wherein the fluorinating agent is potassium fluoride.

[6] The process for producing a fluorinated dicyanobenzene according to [5] wherein the potassium fluoride is prepared by a spray drying method.

[7] The process for producing a fluorinated dicyanobenzene according to claim [5] wherein the potassium fluoride has an average bulk specific gravity of from 0.1 to 0.7 g/ml.

[8] The process for producing the fluorinated dicyanobenzene according to any one of [1] to [7] wherein the fluorinated dicyanobenzene represented by the formula (2) is tetrafluoro phthalonitrile, tetrafluoro isophthalonitrile or tetrafluoro terephthalonitrile.

[9] The process for producing the fluorinated dicyanobenzene according to [8] wherein the fluorinated dicyanobenzene represented by the formula (2) is tetrafluoro terephthalonitrile.

[10] The process for producing the fluorinated dicyanobenzene as described in any one of [1] to [9], which process comprises carrying out the reaction while disintegrating bulk solid matters contained in the reaction mixture and/or while removing bulk solid matters adhered to the wall inside the reaction vessel.

[11] The process for producing the fluorinated dicyanobenzene as described in [10], wherein, in carrying out the reaction while disintegrating bulk solid matters contained in the reaction mixture and/or while removing bulk solid matters adhered to the wall inside the reaction vessel, a mixing machine equipped with a ribbon-shaped and/or screw-shaped stirrer is used.

[12] The process for producing the fluorinated dicyanobenzene as described in [10], wherein, in carrying out the reaction while disintegrating bulk solid matters contained in the reaction mixture and/or while removing bulk solid matters adhered to the wall inside the reaction vessel, any one device of a kneader mixer, internal mixer, muller mixer, crusher, ribbon-shaped mixer, vertical screw-shaped (planetary-shaped) mixer and rotary mixer is used.

[13] The process for producing the fluorinated dicyanobenzene according to any one of [10] to [12], wherein the bulk solid matters are in an amount of not more than 10% by mass based on the total amount of the reaction mixture in carrying out the reaction.

[14] The process for producing the fluorinated dicyanobenzene according to any one of [1] to [13], wherein the reaction temperature is from 80° C. to 200° C.

[15] The process for producing the fluorinated dicyanobenzene, which process comprises the steps of conducting the fluorinating reaction with the process as described in any one of [1] to [14], thereafter cooling a reaction solution to lower than 60° C. and adding water into the reaction solution to crystallize and deposit fluorinated dicyanobenzenes represented by the formula (2).

MODE OF CARRYING OUT THE INVENTION

The present invention will be further described in detail hereinafter.

The tetrachlorodicyanobenzene represented by the formula (1)

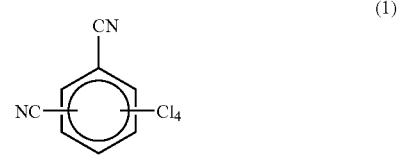
(1)

which is used as a raw material of the invention may include, for example, tetrachloroterephthalonitrile, tetrachloroisophthalonitrile and tetrachloroorthophthalonitrile.

The reaction process of the present invention is carried out by feeding tetrachlorodicyanobenzene, a non-protonic polar solvent in an amount of 0.1 to 3 times by mass based on the tetrachlorodicyanobenzene and a fluorinating agent to a reaction vessel and heating at a prescribed temperature with stirring. After the reaction is completed, the mixture is crystallized and dried to prepare a fluorinated dicyanobenzene of high purity in a high yield.

The fluorinated dicyanobenzene, which is a product of the present invention, is a compound of the formula (2)

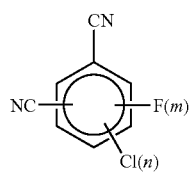

(2)

in which m is an integer of 1 to 4, n is 0 or an integer of 1 to 3, and m+n=4, and may include, for example, trichlorofluorophthalonitrile, trichlorofluoroisophthalonitrile, trichlorofluoroterephthalonitrile, dichlorodifluorophthalonitrile, dichlorodifluoroisophthalonitrile, dichlorodifluoroterephthalonitrile, chlorotrifluorophthalonitrile, chlorotrifluoroisophthalonitrile, chlorotrifluoroterephtthalonitrile, tetrafluorophthalonitrile, tetrafluoroisophthalonitrile and tetrafluoroterephtalonitrile. Preferred examples may include tetrafluorophthalonitrile, tetrafluoroisophthalonitrile, chlorotrifluoroisophthalonitrile and tetrafluoroterephthalonitrile. Further preferred examples may include tetrafluoroterephthalonitrile.

The fluorinated dicyanobenzene, which is a product of the invention, can be mono-fluorine substituent, di-fluorine substituent, tri-fluorine substituent and tetra-fluorine substituent by regulating the amount of the fluorinating agent used in the reaction.

Examples of the fluorinating agent used in the present invention may include alkali metal fluorides or alkaline earth metal fluorides. Examples of the alkali metal fluorides may include potassium fluorides, sodium fluorides, cesium fluorides, rubidium fluorides and lithium fluorides. Examples of the alkaline earth metal fluorides may include barium fluorides and calcium fluorides. These fluorinating agents may be used alone or in combination of two or more. Among the above, easily available commercial potassium fluorides are specially preferred. Particularly, potassium fluorides prepared by the spray drying method (available from Morita Chemicals Inc.) are preferred. Further, among them, potassium fluoride having an average bulk specific gravity of from 0.1 to 0.7 g/ml is effective because it has high reactivity.

The solvent used in the invention is not particularly limited as long as it is a non-protonic polar solvent, and it may be used singly or in a mixture with other solvents. Appropriate examples of the solvent may include N,N-dimethylformamide (DMF), diethylformamide, dimethylsulfoxide (DMSO), dimethylsulfone (DMSO$_2$), sulforane, 2-methyl-2-pyrrolidone, 1,3-dimethyl-2-imidazolidinone, dimethylacetoamide, and benzonitrile. Among them, N,N-dimethylformamide (DMF), dimethylsulfoxide (DMSO) and N-methyl-2-pyrrolidone are preferred.

In the reaction of the present invention, the non-protonic polar solvent is used in an amount of from 0.1 to 3 times by mass, preferably 0.1 to 2 times by mass based on tetrachlorodicyanobenzene which is a starting material. When the non-protonic polar solvent is less than 0.1 times by mass, the reaction rate is slow. When more than 3 times by mass, the yield of the resulting fluorinated dicyanobenzene is low.

The reaction of the present invention is carried out by thoroughly stirring the reaction mixture so that bulk solid matters are not produced in the creamy or wet powdery reaction mixture. While carrying out the reaction of the present invention, when the bulk solid matters are produced in the reaction mixture, or produced and adhered to the wall surface of the reaction vessel, it is preferred that the reaction is carried out while disintegrating or removing these bulk solid matters. In the reaction of the present invention, it is preferred that the amount of bulk solid matters contained in the reaction mixture or adhered to the wall surface of reaction vessel is small.

The term "bulk solid matters" used in the specification means large solid matters, which are adhered to the inner wall of the reactor, or that are not taken out and remain, after the liquid obtained by the reaction has been removed from the reactor. The expression "removing" the bulk solid matters adhered to the wall surface of the reaction vessel means eliminating the bulk solid matters in the state fixed to the wall surface, for example, from the adhered surface, separating, peeling, scratching away or disintegrating. More specifically, examples of the procedure may include scratching away with a stirring blade and removing with application of force.

The mixer used as the reactor of the present invention is not particularly limited as long as it has a function of thoroughly stirring to such an extent that bulk solid matters are not produced in the creamy or wet powdery reaction mixture, or has a function of disintegrating or removing the bulk solid matters produced or adhered to the wall surface of the reaction vessel, and also has a heating mechanism.

As described in the above, the reactor used in the invention has no limitation as long as it has the function of disintegrating or removing the bulk solid matters. For attaining such a purpose it is preferable that the reactor is a device equipped with a stirrer having a ribbon-shaped or screw-shaped spiral blade.

Further, as the mixer having the heating mechanism suitable for the reaction process of the present invention, for example, a mixing device usable for viscosity materials and a device capable of mixing bulk solid materials are effective.

Examples thereof are a mixer designed with a structure such that the gap between the wall surface and the stirring blade is narrow, and a mixing device having a screw that revolves near the wall surface and also rotates. Specific examples thereof may include a kneader mixer, internal mixer, muller mixer, crusher, ribbon-shaped mixer, vertical screw-shaped mixer (planetary-shaped) [Nauta-mixer (Trade Mark Hosokawa Micron CO.) or the like] and rotary mixer.

The fact that these mixers are effective in the reaction of the present invention means that it is unnecessary in the reaction of the invention to enhance the stirring rate and make the whole reaction system uniform, which is different from general reactions. This means that if only the mixing is conducted with disintegrating or removing bulk solid matters in order to prevent production of large amounts of bulk solid matters, the reaction proceeds. That is, it indicates that the reaction system has to only flow partly, but the whole does not need to be uniform. In usual reactions, even in solid-liquid reactions, it is usual to conduct stirring so that the whole is uniform. Therefore, the reaction conditions of the present invention are hardly expected from common knowledge.

The amount of the bulk solid matters produced in the reaction mixture or adhered to the wall surface of the reaction vessel according to the present invention is preferably not higher than 10% by mass based on the whole reaction mixture. When the amount is over 10% by mass, the reaction rate lowers, and further, the yield of fluorinated dicyanobenzene and the purity thereof lower.

In the case the reaction is continuously carried out with one reactor, if the amount of the bulk solid matters produced in the reaction mixture and adhered to the wall surface of the reaction vessel is not more than 10% by mass based on the whole reaction mixture, the reaction may be carried out with the bulk solid matters remained inside the reactor and thereby particularly has no problems.

When the reaction mixture contains a large amount of water, there is a problem that the reaction rate decreases and the yield lowers, so that the amount of the water is preferably small. Therefore, it is preferred that the water amount in the raw materials including the fluorinating agent, solvent and terachlorodicyanobenzene is small. Further, it is effective for the reaction to design a device to avoid moisture absorption or the like in feeding the raw materials, and to partly distill the solvent and then dehydrate after feeding the raw materials. In some cases, it is also effective to distill and dehydrate by adding other water-azeotropic components.

In the present invention, the yield is increased by using the solvent in an amount of less than 3 times by mass based on the raw material tetrachlorodicyanobenzene. It is considered that one reason is because the moisture contaminated in the reaction system is easily depressed by decreasing the solvent amount used.

The reaction of the present invention is carried out at a reaction temperature of from room temperature to 200° C., preferably 80 to 200° C.

The reaction time varies depending on the reaction temperature or the kind of objective fluorinated dicyanobenzene, and may be usually less than 10 hours.

In the present invention, the reaction may be carried out in the presence of a phase transfer catalyst. Examples of the phase transfer catalyst may include a quaternary phosphonium salt, quaternary ammonium salt, crown ether and polyalkylene glycol.

The fluorinated dicyanobenzene, which is a product of the present invention, can be isolated by, for example, crystallization, distillation, extraction, two-phase separation and sublimation. Among the methods, crystallization by adding water into the reaction mixture after the reaction is completed is effective. In the case of carrying out the crystallization by adding water, it is preferred that the reaction mixture be cooled to lower than 60° C. before adding water because when the reaction solution temperature is high, the fluorinated dicyanobenzene product decomposes to decrease the yield and the purity of the resulting products. For example, in the preparation of tetrafluoroterephthalonitrile from tetrachloroterephthalonitrile and potassium fluoride in the presence of a N,N-dimethylformamide solvent, tetrafluoroterephthalonitrile having high purity of not less than 97% can be easily isolated in such a way that the solution obtained after the reaction is cooled to lower than 60° C., then water is added in an amount of about 2.1 times by mass based on the used solvent to the solution, and the water solution is subjected to crystallization and filtration, and the resulting crystals are dried.

Effect of the Invention

According to the present invention, fluorinated dicyanobenzenes having high purity useful as an intermediate and raw material for preparation of medical and pharmaceutical products, agricultural chemicals and polymers can be produced in a high yield by industrially profitable methods.

EXAMPLES

The present invention will be described with reference to the examples hereinafter.

<Analysis conditions>

The analysis conditions of liquid chromatography and gas chromatography employed in the examples are as follows.

(Analysis conditions of liquid chromatography)

| Device: | Shimazu LC-10 |
|---|---|
| Column: | Shodex ODSpak F-511 (Particle diameter 5 μm, Size 4.6 mm (diameter) × 150 mm (length)) |
| Eluting solution: | Acetonitrile/water = 40/60 |
| Flow rate: | 1 ml/min |
| Detector: | UV (242 nm) |
| Column temperature: | 50° C. |
| Injection: | 5 μL |

(Analysis conditions of gas chromatography)

| Device: | Agilent 6890 |
|---|---|
| Column: | Agilent J&W DB-1 (Size 30 m (length) × 0.53 mm (diameter) × 1.5 μm (film thickness)) |
| Carrier: | Helium, 5.6 mL/min constant flow |
| Injection: | Split (10:1), 1 μL, Inlet 300° C. |
| Oven: | (1) 80° C. → 200° C. (5° C./min) |
| | (2) 200° C. → 290° C. (15° C./min) |
| | (3) 290° C. (5 min) |
| Detector: | FID 300° C. |
| Internal standard substance: | o-dichlorobenzene |
| Diluting solvent: | Acetone |

Example 1

Into a 1 L cylindrical flask, 210 g of tetrachloroterephthalonitrile having a purity of 98.35%, 205 g of potassium fluoride having an average bulk specific gravity of 0.5 g/ml prepared by the spray drying method and 475 g of N,N-dimethylformamide having a water content of 100 ppm as a solvent were charged, and while stirring them with a large-sized stirrer having ribbon blade in a nitrogen atmosphere, the temperature was elevated using an oil bath heated at 130° C. From the time at which the internal temperature reached 115° C., the reaction was continued for 4.5 hr. Thereafter, the reaction solution was cooled to 60° C., and transferred into a 2 L round flask. The mass of bulk solid matters, which were adhered to the wall surface of the reactor during the reaction and remained after the transfer of the reaction solution, was 42.75 g (this mass corresponds to 4.8% of the all reaction solution mass). After all of the reaction solution was transferred, 1018 g of water was introduced into the reaction solution while stirring for 40 min, and thereby the potassium chloride deposited was mostly dissolved and also crystals of tetrafluoroterephthalonitrile were deposited. The crystals were separated by a Nutsche funnel, and were washed with 400 g of water at 40° C. When analyzed by liquid chromatography and evaluated, the total amount of tetrafluorophthalonitrile present in the filtrate filtered and the washing water was 0.21 g (this amount corresponds to 0.14% of the yield based on tetrachloroterephthalonitrile). The resulting crystals were dried with a vacuum dryer at 60° C. to obtain 146.2 g of dried crystals. When analyzed by gas chromatography, the crystals were found to be tetrafluoroterephthalonitrile having a purity of 99.1%. The yield based on the tetrachloroterephthalonitrile was 93.2%.

Example 2

The procedure of Example 1 was repeated except the amount of N,N-demethylformamide used was changed to 420 g. 147.1 g of dried crystals of tetrafluoroterephthalonitrile having a purity of 99.0% was prepared. The yield based on the tetrachloroterephthalonitrile was 93.7%.

Example 3

The procedure of Example 1 was repeated except the amount of N,N-dimethylformamide used was changed to 630 g. 143.2 g of dried crystals of tetrafluoroterephthalonitrile having a purity of 99.0% was prepared. The yield based on the tetrachloroterephthalonitrile was 91.2%.

Example 4

Into a 20 L glass reactor, 2.40 kg of tetrachloroterephthalonitrile having a purity of 98.35%, 2.34 kg of potassium fluoride having an average bulk specific gravity of 0.5 g/ml prepared by the spray drying method and 5.43 kg of N,N-dimethylformamide having a water content of 100 ppm as a solvent were charged, and while stirring them with a stirrer having a turbine blade, the temperature was elevated using an oil bath. During the reaction, because bulk solid matters were adhered to the wall surface of the reactor, the reaction was carefully carried out with occasional changes in stirring velocity so that the bulk solid matters were not adhered to the utmost. From the time at which the internal temperature reached 115° C., the reaction was continued for 4.5 hr. Thereafter, the reaction solution was cooled to 60° C., and transferred into a 20 L vessel. When estimated from the mass of the reaction solution transferred, it was considered that the mass of bulk solid matters, which were adhered to the wall surface of the reactor during the reaction and remained after the transfer of the reaction solution, was about 1.01 kg. (this mass corresponds to 9.9% of the all reaction solution mass). After all of the reaction solution was transferred, 11.63 kg of water was introduced into the solution while stirring for 40 min, and thereby the potassium chloride deposited was mostly dissolved and also crystals of tetrafluoroterephthalonitrile were deposited. The deposited crystals were separated by a Nutsche funnel, and were washed with 2.28 kg of water at 40° C. When analyzed by liquid chromatography and evaluated, the total amount of tetrafluoroterephthalonitrile present in the filtrate filtered and the washing water was 0.002 kg (the amount corresponds to 0.11% of the yield based on tetrachloroterephthalonitrile). The resulting crystals were dried with a vacuum dryer at 60° C. to obtain 1.56 kg of dried crystals. When analyzed by gas chromatography, the crystals were found to be tetrafluoroterephthalonitrile having a purity of 98.8%. The yield based on the tetrachloroterephthalonitrile was 86.8%.

Example 5

Into a 2.5 m$^3$ vertical screw-shaped (planetary-shaped) mixer, 420 kg of tetrachloroterephthalonitrile having a purity of 98.35%, 410 kg of potassium fluoride having an average bulk specific gravity of 0.5 g/ml prepared by the spray drying method and 950 kg of N,N-dimethylformamide having a water content of 100 ppm as a solvent were charged, and while stirring them with a stirrer at 60rotations per minute and 0.8 revolution per minute in a nitrogen atmosphere, the temperature was elevated by passing steam at 3 kg/cm$^2$ to a jacket. From the time at which the internal temperature reached 115° C., the reaction was continued for 4.5 hr. Thereafter, the reaction solution was cooled to 60° C., and transferred into a 3.5 m$^3$ crystallization bath using a slurry pump. Just after the reaction solution was transferred, 2036 kg of water was introduced for 40 min, and thereby the potassium chloride deposited was mostly dissolved and also crystals of tetrafluoroterephthalonitrile were deposited. The deposited crystals were separated by a centrifugal filter, and were washed with 400 kg of water at 40° C. Thereafter the crystals were dried with a conical dryer to obtain 292.3 kg of dried crystals. When analyzed by gas chromatography, the crystals were found to be tetrafluoroterephthalonitrile having a purity of 99.0%. The yield based on the tetrachloroterephthalonitrile was 93.1%.

Example 6

The procedure of Example 5 was repeated except that the amount of N,N-dimethylformamide used was changed to 760 kg. 296.1 kg of dried crystals of tetrafluoroterephthalonitrile having a purity of 99.0% was prepared. The yield based on the tetrachloroterephthalonitrile was 94.3%.

Comparative Example 1

Into a 20 L glass reactor, 2.03 kg of tetrachloroterephthalonitrile having a purity of 98.35%, 2.62 kg of potassium fluoride having an average bulk specific gravity of 0.5 g/ml prepared by the spray drying method and 14.16 kg of N,N-dimethylformamide having a water content of 100 ppm as a solvent were charged, and while stirring them with a stirrer having a turbine blade, the temperature was elevated using an oil bath. From the time at which the internal temperature reached to 130° C., the reaction was continued for 5 hr. Thereafter, the reaction solution was introduced to a 50 L vessel containing 33.05 kg of iced water. The potassium chloride deposited was mostly dissolved and also crystals of tetrafluoroterephthalonitrile were deposited. The deposited crystals were separated by a Nutsche funnel, and were washed with 1.73 kg of water at 40° C. When analyzed by liquid chromatography and evaluated, the total amount of tetrafluorophthalonitrle present in the filtrate filtered and the washing water was 0.005 kg. (the amount corresponds to 0.3% of the yield based on tetrachloroterephthalonitrile). The resulting crystals were dried with a vacuum dryer at 60° C. to obtain 1.22 kg of dried crystals. When analyzed by gas chromatography, the crystals were found to be tetrafluoroterephthalonitrile having a purity of 99.0%. The yield based on the tetrachloroterephthalonitrile was 80.4%.

The invention claimed is:

1. A process for producing a fluorinated dicyanobenzene represented by the formula (2):

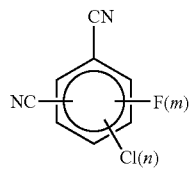

wherein m is an integer of 1 to 4, n is 0 or an integer of 1 to 3, and m+n=4, wherein the process comprises reacting a tetrachlorodicyanobenzene represented by the formula (1)

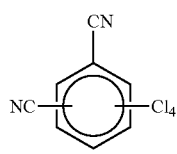

with a fluorinating agent in the presence of a non-protonic polar solvent in an amount of from 0.1 to 3 times by mass based on said tetrachlorodicyanobenzene, wherein the reaction is carried out while disintegrating bulk solid matters contained in a reaction mixture and/or while removing bulk solid matters adhered to a wall inside a reaction vessel.

2. The process for producing a fluorinated dicyanobenzene according to claim 1, wherein the non-protonic polar solvent is an organic solvent comprising at least one selected from the group consisting of N,N-dimethyl formamide, dimethyl sulfoxide and N-methyl-2-pyrrolidone.

3. The process for producing a fluorinated dicyanobenzene according to claim 1, wherein the non-protonic polar solvent is N,N-dimethyl formamide.

4. The process for producing a fluorinated dicyanobenzene according to claim 1, wherein the fluorinating agent is an alkali metal fluoride or alkaline earth metal fluoride.

5. The process for producing a fluorinated dicyanobenzene according to claim 4, wherein the fluorinating agent is potassium fluoride.

6. The process for producing a fluorinated dicyanobenzene according to claim 5, wherein said potassium fluoride is prepared by a spray drying method.

7. The process for producing a fluorinated dicyanobenzene according to claim 5, wherein said potassium fluoride has an average bulk specific gravity of from 0.1 to 0.7 g/ml.

8. The process for producing a fluorinated dicyanobenzene according to claim 1, wherein the fluorinated dicyanobenzene represented by the formula (2) is tetrafluoro phthalonitrile, tetrafluoro isophthalonitrile or tetrafluoro terephthalonitrile.

9. The process for producing a fluorinated dicyanobenzene according to claim 8, wherein the fluorinated dicyanobenzene represented by the formula (2) is tetrafluoroterephthalonitrile.

10. The process for producing a fluorinated dicyanobenzene according to claim 1, wherein, in carrying out the reaction while disintegrating bulk solid matters contained in the reaction mixture and/or while removing bulk solid matters adhered to the wall inside the reaction vessel, a mixing machine equipped with a ribbon-shaped and/or screw-shaped stirrer is used.

11. The process for producing a fluorinated dicyanobenzene according to claim 1, wherein, in carrying out the reaction while disintegrating bulk solid matters contained in the reaction mixture and/or while removing the bulk solid matters adhered to the wall inside the reaction vessel, any one device of a kneader mixer, internal mixer, muller mixer, crusher, ribbon-shaped mixer, vertical screw-shaped (planetary-shaped) mixer and rotary mixer is used.

12. The process for producing a fluorinated dicyanobenzene according to claim 1, wherein the bulk solid matters are in an amount of not more than 10% by mass based on the total amount of the reaction mixture in carrying out the reaction.

13. The process for producing a fluorinated dicyanobenzene according to claims 1, wherein the reaction temperature is between 80° C. and 200° C.

14. A process for producing a fluorinated dicyanobenzene, which process comprises the steps of conducting a fluorinating reaction by the process as claimed in claim 13, thereafter cooling a reaction solution to lower than 60° C. and adding water to crystallize and deposit a fluorinated dicyanobenzene represented by the formula (2).

* * * * *